United States Patent
Camilli

Patent Number: 5,607,465
Date of Patent: Mar. 4, 1997

[54] PERCUTANEOUS IMPLANTABLE VALVE FOR THE USE IN BLOOD VESSELS

[76] Inventor: Sante Camilli, Via Casale D'Elsa, 15, 00139-Roma, Italy

[21] Appl. No.: 300,133

[22] Filed: Sep. 2, 1994

[30] Foreign Application Priority Data

Dec. 14, 1993 [EP] European Pat. Off. ............. 93830500

[51] Int. Cl.⁶ .................................................... A61F 2/06
[52] U.S. Cl. ................................. 623/1; 623/2; 623/11; 623/66; 623/12; 604/93; 604/104; 604/264; 604/96; 606/108; 606/195
[58] Field of Search ................................. 623/1–2, 11–12, 623/66; 137/512.1, 527, 527.8; 604/104, 93, 96, 264; 606/108, 195

[56] References Cited

U.S. PATENT DOCUMENTS

| | | | |
|---|---|---|---|
| 3,714,671 | 2/1973 | Edwards et al. | 623/2 |
| 4,056,854 | 11/1977 | Boretos et al. | |
| 4,605,407 | 8/1986 | Black et al. | 623/2 |
| 5,037,434 | 8/1991 | Lane | 623/2 |

FOREIGN PATENT DOCUMENTS

| | | |
|---|---|---|
| 0030826 | 6/1981 | European Pat. Off. . |
| 0520126 | 12/1992 | European Pat. Off. . |
| 4101935 | 7/1992 | Germany . |
| 2164562 | 3/1986 | United Kingdom ....................... 623/1 |
| WO91/17720 | 11/1991 | WIPO . |
| WO93/01768 | 2/1993 | WIPO . |

Primary Examiner—David Isabella
Assistant Examiner—P. Zuttarelli
Attorney, Agent, or Firm—Young & Thompson

[57] ABSTRACT

A valve for use in a blood vessel, internal to the blood vessel itself, in contact with a blood stream, has a bent flexible wire mesh (1) with elasticity and plasticity so as to be collapsible and implantable remotely at a desired site. The wire mesh (1) is bent into three turns, two end ones (6, 6') and a central one (5), in such a way as to confine a tubular space. The central turn (5) is located at an angle relative to the end turns (6, 6') and mounts a monocusp sail-like valving element (2). A special catheter (12) is used to collapse the flexible wire mesh (1), to implant it remotely at the desired site, and to restore the wire mesh (1) to its original three-dimensional configuration.

7 Claims, 3 Drawing Sheets

PERCUTANEOUS IMPLANTABLE VALVE FOR THE USE IN BLOOD VESSELS

FIELD OF THE INVENTION

The present invention relates to valves for use in living bodies.

More particularly, it relates to artificial valves for use in a blood vessel, internal to the blood vessel itself, in contact with the blood stream passing therethrough.

Still more particularly, though not exclusively, the present invention relates to valves which are intended to operate inside a vein with a monocusp valving element.

As used herein, a "valving element" or "valving means" is mounted on the support of the valve, whereby the control of the blood flow is achieved.

The present invention also relates to a catheter for implanting such a valve into a blood vessel.

BACKGROUND OF THE INVENTION

There is not any artificial valve implantable remotely by catheter for use in blood vessels available up to the present day.

Moreover, there is not any artificial valve for use in veins commercially available up to the present day, notwithstanding some specific attempts, such as those valves disclosed by Lane (International Application Number PCT/AU87/00220), Taheri (International Application Number PCT/US88/03175) and Quijano et al. (PCT/US90/03053).

The main problem with such valves is the ease of thrombosis, which immobilizes the valve and, therefore, prevents it from operating, More specifically, Lane's valve is not, strictly speaking, a valve, but only an outer prosthesis whereinto a vein segment is intussuscepted to form a venous valve, in which the blood does not come in contact with the prosthesis itself. It is not commercially available, and it is not implantable remotely by a catheter.

Taheri's valve has an annular support which has a tendency to go out of alignment when implanted in a vein during low endoluminal pressure stages and when the vein is compressed From the outside. Its valving means are two leaflets, which are not protected by the annular support during their motion of opening and closing from the collapse of the venous wall during low endoluminal pressure stages and when the vein is compressed from the outside. It is not commercially available, it is not implantable remotely by a catheter.

Quijano et al.'s valve is a biological valve, i.e. it is entirely made from animal tissues, and has a two-leaflet valving means. It is not commercially available, and it is not implantable remotely by a catheter.

Various types of artificial valves made for use in hearts (i.e. heart valves) are known in the operative art: these valves are not applicable in veins. In fact, they are intrinsically different from venous valves various reasons, e.g. structure, size, materials or the characteristics of mechanical strength the forces necessary for their operation, the way of insertion, or the method fop fixing them in the desired site. In the heart and in the vessels connected therewith, there are high pressures and high instantaneous flows; moreover, the vessels have large diameters and are protected against compression from the outside by virtue of being positioned inside the thorax. On the contrary, in veins there are low pressures and low flows; moreover, the diameters of the veins that have valvular incompetence are small and these veins are easily compressible from outside under various conditions.

In order to provide an artificial valve that could operate in a vein, the same Applicant hereof suggested in Italian Patent Application Ser. No. RM91A000458 on the 25$^{th}$ Jun., 1991, a valve configured to allow unidirectional flow, biocompatible with veins, comprising a hollow elongated support having a predetermined length with a periphery and a predetermined width, said length being greater than said width, said support having means for fixing itself to a vein, and a plate carried by and within the support and movable relative to the support between a first position to allow flow of blood in one direction and a second position to prevent flow of blood in an opposite direction through said support, said plate being disposed entirely within said support in both of said first and second positions.

Such a valve has only one valving element, as this is made up of the plate, which is a monocusp; so thrombogenesis is substantially reduced and the valve is able to operate reliably.

The fact that the valving element is always inside said support during its motion ensures that it is always protected against the collapse of the vein during low pressure stages.

The main object of the present invention is to provide a valve for use in blood vessels, which is implantable remotely by catheter.

Another object of the present invention is to provide a valve for use in blood vessels, which is substantially less thrombogenic than the known ones.

Such objects are achieved, according to the teaching of the present invention, by utilizing a suitably bent flexible wire having elasticity and plasticity as the support of the valving means.

As used herein "having elasticity and plasticity" means that said wire is plastically de formed when twisted into turns by an operator, but reacts elastically to the forces applied to it by the wall of a blood vessel, particularly a vein, once implanted in the blood vessel itself.

The advantages offered by the present invention are mainly that it provides a valve for use in blood vessels and that is implantable remotely by catheter, which was never done before. This advantage is achieved by virtue of the cage structure of the wire support, which can be so made, as to be folded in such a way as to free its three-dimensional space occupation. After introduction at a remote distance, percutaneously, of the valve into the desired site, the valve itself can be restored to its original three-dimensional configuration.

Moreover, the present invention affords a valve which is substantially less thrombogenic than the known ones: indeed, its support does not develop bidimensionally, by virtue of its cage structure; then it offers a very restricted extension for the formation of thrombi.

SUMMARY OF THE INVENTION

Therefore, the present invention relates to a valve for the use in a blood vessel, internal to the blood vessel itself, in contact with the blood stream, having a support and valving means, characterized in that said support comprises a bent flexible wire having elasticity and plasticity, so as to be implantable remotely by a catheter in a desired site.

According to an embodiment of the present invention, said wire is bent into three turns, i.e. two end ones and a central one, in such a way as to confine a tubular space, said central turn being at an angle relative to said end turns and mounting a monocusp of a sail-like valving element, so that said valving element is protected against the collapse of the blood vessel wall in all of its positions.

It is provided that said sail-like valving element has a check line fixed to said central turn, in order to prevent the valving element itself from stopping in an arbitrary position.

It is also provided that said sail-like valving element has a control shaft incorporated in itself, again to prevent the valving element from stopping in an arbitrary position.

It is also provided that the valve of the present invention has hooking means for its fixation to a blood vessel wall.

The present invention also relates to a catheter having at its distal end a capsule for transporting, means for grasping and loading into said capsule as well as for releasing in a desired site a valve according to the present invention.

It is provided that such a catheter comprises an inflatable balloon to obtain the occlusion of a blood vessel.

BRIEF DESCRIPTION OF THE DRAWINGS

The present invention will be best understood on the basis of the following disclosure of its preferred embodiment, given only as a matter of example and not of restriction, with reference to the annexed drawings, wherein.

DETAILED DESCRIPTION OF THE PREFERRED EMBODIMENT

Figure 1:
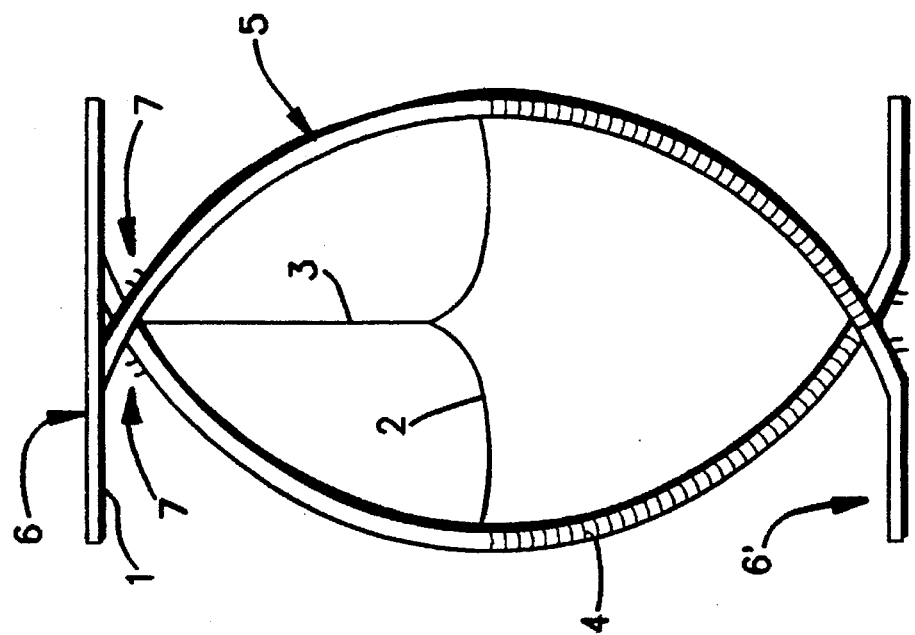
FIG. 1 is a side view of an artificial valve according to the present invention, in its closure position.
Figure 2:
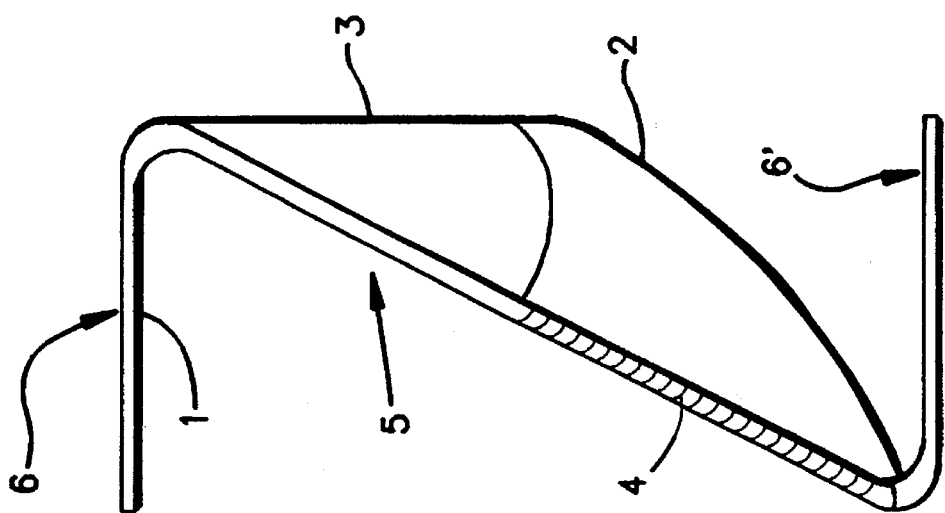
FIG. 2 is a front view of the same.
Figure 4:
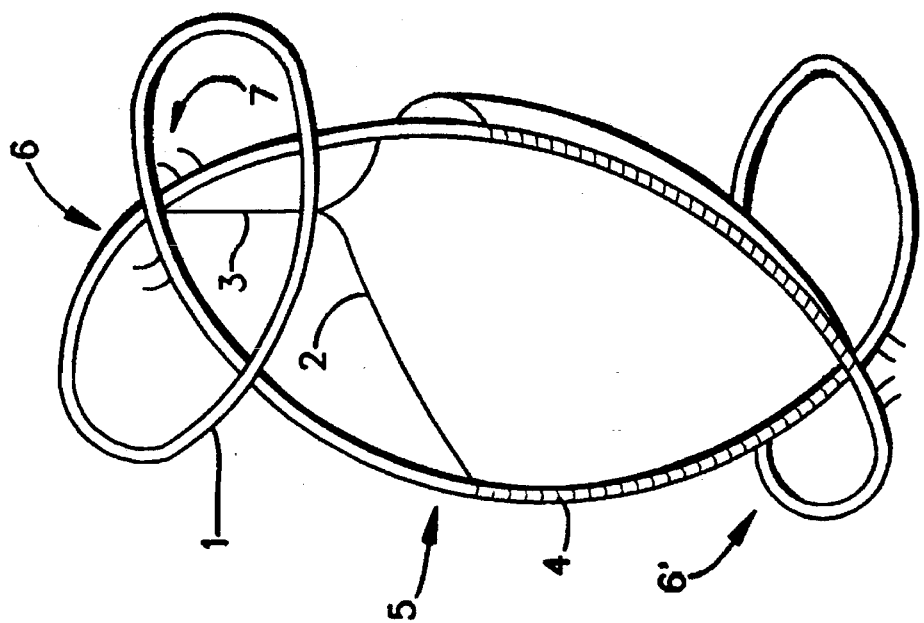
FIG. 4 is a perspective view from the top of the valve.

The support or valve body 1 is made up of a wire mesh 1, in a plastic material or in a biocompatible metallic alloy, such as the nickel (Ni) and cobalt (Co) alloy Phynox®, eventually treated by antithrombogenic processes, having a circular cross section, with a diameter of about 0.3 millimeters, flexible, elastic and plastic, shaped and twisted so as to form three turns, of which there are two end ones 6, 6', substantially circular and lying on the periphery of the bases of a right cylinder, and a central one 5, with an ellipse-like contour substantially lying on a plane at about 130° relative to said circle-like turns 6, 6'.

The so shaped valve body 1 gives the valve a cylinder cage configuration.

It is provided that the base of such a cylinder has a diameter of 6 to 14 millimeters and a height of 15 to 25 millimeters, the sizes being variable in connection with the veins whereinto the valve is to be positioned.

Figure 3:
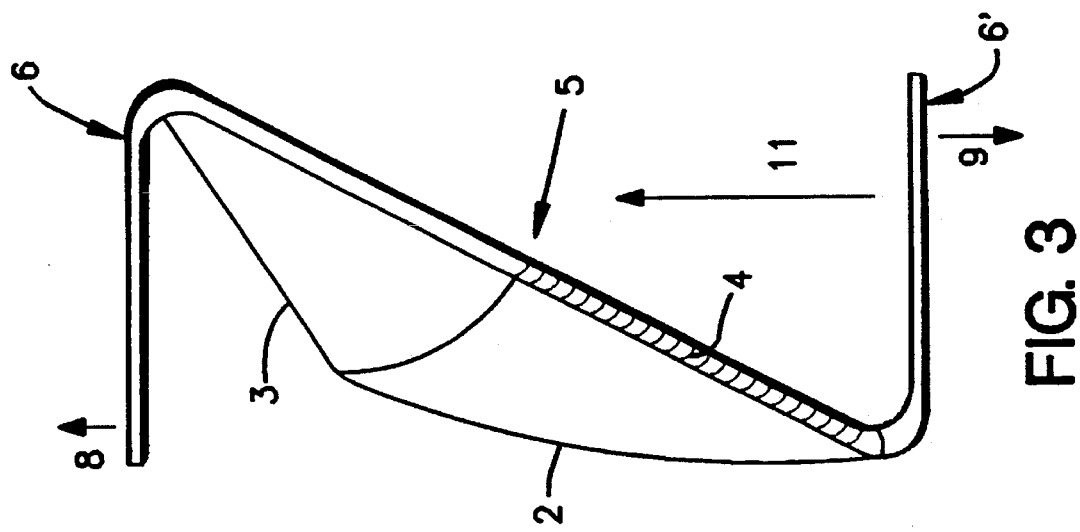
FIG. 3 is a side view of the valve, in its opening position.

Once a suitably sized valve has been inserted into a vein, the ellipse-like turn or main turn, 5 goes to assume an oblique position relative to the direction of the blood stream 11 FIG. 3, while the other two, circle-like turns 6, 6' will assume a position substantially perpendicular to it.

The function of the main, ellipse-like turn 5 is to constitute the support for anchoring a mobile plate or valving element 2.

The function of the two end turns 6, 6' is to keep the main turn 5 in the desired position and to impede a permanent collapse of the vein segment that contains the valve during low endoluminal pressure stages or after extrinsic compression, causing the redistension of the venous segment by means of the elastic reaction of the material which all the valve body is made up of.

The so configured support or valve body 1 is fit for being easily deformed, by applying a traction upon the two end turns 6, 6', thus obtaining the movement indicated with the arrows 8 and 9 in FIG. 3 so that it causes a temporary and incomplete linearization, or decrease of its space occupation and increase of the occupied length of the valve. Under these conditions, the valve can be loaded into a carrying capsule 13 of an introducing catheter shown in with FIGS. 5a to 5c.

Subsequently, during its release and anyhow after any eventual deformation for extrinsic compression, the valve is able to return to its original shape.

The support or valve body 1 has suitable hooks 7, arranged on one or more points of the three turns which it is made up of, having the aim of fixing into the wall of the vein after the release and the positioning of the valve, to prevent its accidental mobilization.

The mobile plate or sail-like valving element 2 is made up of a plastic material, for instance expanded polytetrafluoroethylene, polyurethane, silicone, or a homologous biologic material, such as instance pericardium, eventually treated by one of the processes with an antithrombogenic aim, as a thin plate, for instance 0.1 to 0.3 millimeters. The mobile plate is comprised of a sail, see FIGS. 1 to 4. It is connected with the ellipse-like central turn 5 by means of a biocompatible, essentially non thrombogenic suture thread 4 commonly used in vascular surgery, or by another process fit for obtaining the fixation between the two elements. The turn 5 can be reinforced or anchored in various ways at one or more points of its free edge for the purposes of making a correct closure position thereof and of preventing its stopping in an arbitrary position.

In the present embodiment, the sail-like valving element 2 has a check line 3 anchored to the turn 5 to this end, but it could also have an incorporated control shaft (not shown).

The mobile plate 2 of the valving element is freely floating within the venous lumen and is moved by the pressure gradient on the two surfaces of the same. In the stage of muscular systole, when the pressure on its distal surface is greater than that on its proximal surface, the mobile plate lifts itself and assumes the opening position as in FIG. 3. With the valve body 1 in this position, the blood stream 11 is directed towards the heart. In the stage of muscular diasrole, when the pressure of the blood upon the proximal surface is greater than that on the distal surface, the mobile plate returns to the closure position as shown, as in FIG. 1, and the backflow in the distal direction is stopped. The return to the correct closure position is rendered easier by the presence of the reinforcement and anchoring check line 3, which keeps the mobile plate in the most effective position for the whole operation of the valve.

Having disclosed a valve according to the teaching of the present invention, an instrument for introducing and positioning it into a vein is now disclosed.

Figure 5C:
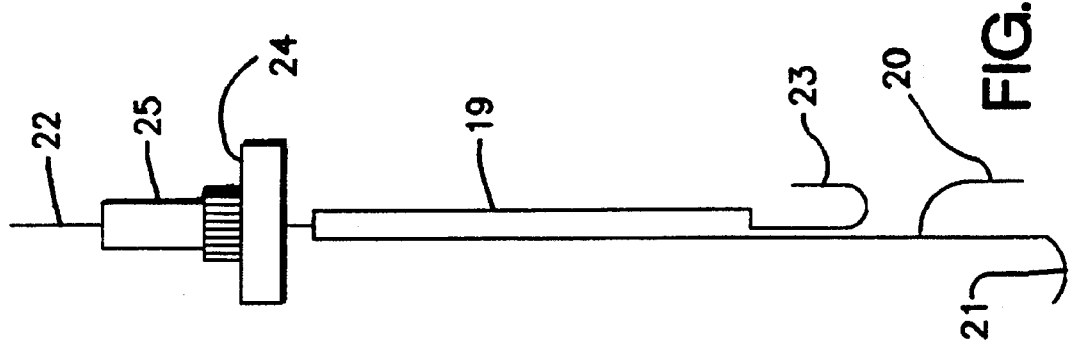
FIGS. 5a to 5c show a catheter for implanting the above valve into a vein.
Figure 5B:
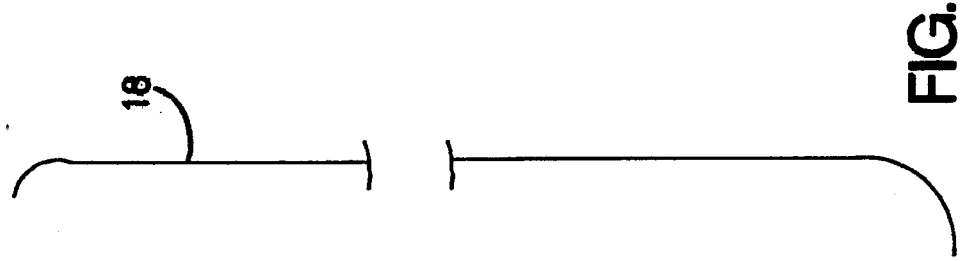
Figure 5A:
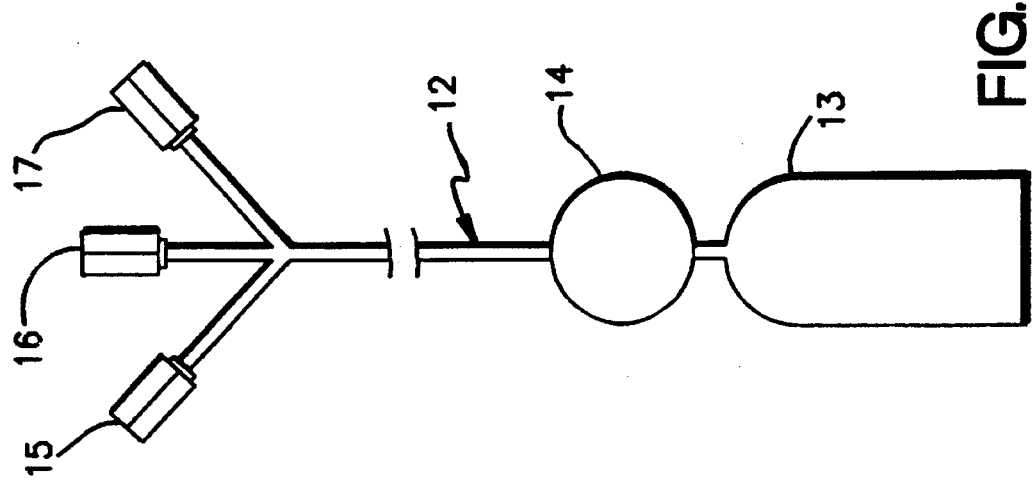

Such an instrument is comprised of the introducing catheter, shown in FIGS. 5a to 5c.

This latter is made up of:

a tubular catheter 12 formed from a plastic material, for instance polyethylene or silicone, of a suitable diametre for the use of two operative ways;

the end carrying capsule 13, made of a metal or a plastic material, of a suitable hardness and antiadherence, of a suitable diameter (10 to 15 F.), being hollow at its interior and ending with an opening extended to all of its diameter, fitted for housing the valve according to the present invention during the transport maneuver from the exterior to the interior of the vein, up to the established point;

an inflatable balloon 14, arranged upstream of the capsule 13, with a connection channel coaxial with the operative one and having a Luer lock connector 15, suitable for obtaining the stopping of the venous circulation and thus useful to render the angioscopic and angiographic check easier during and after the positioning of the valve;

a flexible guide 18, of the type in use in angiography, which can be introduced into the catheter 12a through the connector 17, suitable during the stage of introduction of said catheter 12, and a maneuverable instrument shown in FIG. 5c, which can be introduced into the catheter 12 through an entrance 16, for grasping the valve during both the stage of loading it into the interior of the transport capsule 13 and the stage of releasing it into the vein. The instrument is made up of a stiff guide 19 having at its extremity a suitable instrument 20 for fixing the valve and also having a very flexible and delicate termination point 21 with a guide 22, coaxial with the preceding one. There is also provided a suitable instrument 23 for grasping the valve. This instrument 2 slideable in two opposite senses relative to the guide 19. There is also a radial check and positioning reference 24 with a screw or sliding system (25) fit for producing the movement of pulling or pushing of the guide line 22 and the instrument 23 relative to the stiff guide 19 with it's termination point 21.

The catheter 12, after placing the valve body 1 into the interior of the capsule 13 by exploiting its flexibility features, is introduced into the venous lumen and allows the transport of the valve body 1 intraluminal way to the desired point where finally its release and definitive positioning take place.

The positioning takes place under the inspection of the surgeon's view or under fluoroscopic monitoring or by any other method.

The fixing of the valve body 1 into its correct position, in the interior of the vein, can be achieved by means of direct suture points, applied from the exterior onto the venous wall and hooked in one or more points of the valve body 1, or through the fixing into the venous wall of the proper hooks 7 on the valve body 1. In the latter case, the valve body 1 still can be repositioned or removed and eventually substituted through a percutaneous way, with a process analogous to that of introduction remotely by catheter.

The present invention has been disclosed with reference to a specific embodiment thereof, but it is to be understood that additions, omissions and/or changes can be made, without departing from its scope of protection, defined by the appended claims.

I claim:

1. A valve for use in a blood vessel, internal to the blood vessel itself, in contact with a blood stream, comprising:

a bent flexible wire having elasticity and plasticity so as to be resilient, self-expanding and implantable remotely at a desired site;

wherein said wire is bent into at least three turns, to confine a tubular space, said at least three turns including a central turn and two end turns, said central turn being at an angle relative to said end turns; and a monocusp valving element mounted on the central turn.

2. The valve according to claim 1, wherein the valving element has a check line fixed to said central turn.

3. A valve for use in a blood vessel, internal to the blood vessel itself, in contact with a blood stream, comprising:

a bent flexible wire having elasticity and plasticity so as to be resilient, self-expanding and implantable remotely at a desired site;

wherein said wire is bent into at least three turns, to confine a tubular space, said at least three turns including a central turn and two end turns, said central turn being at an angle relative to said end turns;

a monocusp valving element mounted on the central turn; and hooking means for fixing the wire to a blood vessel wall.

4. A valve for use in a blood vessel, internal to the blood vessel itself, in contact with a blood stream, comprising:

a bent flexible wire having elasticity and plasticity so as to be resilient, self-expanding and implantable remotely at a desired site;

wherein said wire is bent into at least three turns, to confine a tubular space, said at least three turns including a central turn and two end turns, said central turn being at an angle relative to said end turns;

a monocusp valving element mounted on the central turn; and means for preventing the valving element from stopping in an arbitrary position other than the desired site in the blood vessel.

5. The valve according to claim 4, wherein the preventing means comprises a check line anchored to said central turn.

6. A catheter comprising:

means for folding a valve body (1) from an original three-dimensional configuration into a temporary and linear form, a capsule means (13) for transporting the valve body (1) into a blood vessel, means (19 to 25) for grasping and loading the valve body (1), into said capsule means (13), means for releasing the valve body (1) at a desired site, and means for restoring the valve body (1) to the original three-dimensional configuration.

7. The catheter according to claim 6, further comprising:

an inflatable balloon (14) to obtain the occlusion of a blood vessel.

* * * * *